United States Patent
Li

(10) Patent No.: US 11,273,030 B2
(45) Date of Patent: Mar. 15, 2022

(54) ELEVATED OUTER CUFF FOR REDUCING PARAVALVULAR LEAKAGE AND INCREASING STENT FATIGUE LIFE

(71) Applicant: St. Jude Medical, Cardiology Division, Inc., St. Paul, MN (US)

(72) Inventor: Xue Mei Li, Shoreview, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 51 days.

(21) Appl. No.: 16/706,953

(22) Filed: Dec. 9, 2019

(65) Prior Publication Data

US 2020/0205967 A1    Jul. 2, 2020

Related U.S. Application Data

(60) Provisional application No. 62/784,823, filed on Dec. 26, 2018.

(51) Int. Cl.
*A61F 2/24* (2006.01)

(52) U.S. Cl.
CPC .......... *A61F 2/2409* (2013.01); *A61F 2/2418* (2013.01); *A61F 2220/0075* (2013.01); *A61F 2250/007* (2013.01); *A61F 2250/0069* (2013.01)

(58) Field of Classification Search
CPC ............ A61F 2/2418; A61F 2250/0069; A61F 2220/0075
See application file for complete search history.

(56) References Cited

U.S. PATENT DOCUMENTS

| 3,657,744 A | 4/1972 | Ersek |
| 4,275,469 A | 6/1981 | Gabbay |

(Continued)

FOREIGN PATENT DOCUMENTS

| DE | 19857887 A1 | 7/2000 |
| DE | 10121210 B4 | 11/2005 |

(Continued)

OTHER PUBLICATIONS

"Catheter-Implanted Prosthetic Heart Valves: Transluminal Catheter Implantation of a New Expandable Artificial Heart Valve in the Descending Thoracic Aorta In Isolated Vessels and Closed Chest Pigs", Knudsen et al., The International Journal of Artificial Organs, vol. 16, No. 5, May 1993, pp. 253-262.

(Continued)

*Primary Examiner* — Suba Ganesan
(74) *Attorney, Agent, or Firm* — Lerner, David, Littenberg, Krumholz & Mentlik, LLP

(57) ABSTRACT

A prosthetic heart valve may include a valve assembly disposed within a stent, and first and second cuffs. The stent may extend in a longitudinal direction from an inflow end to an outflow end. The first cuff may be annularly disposed adjacent the stent. The second cuff may have a proximal edge facing toward the inflow end of the stent and a distal edge facing toward the outflow end of the stent. The second cuff may be annularly disposed about the stent radially outward of the first cuff. The distal edge of the second cuff may be coupled to the first cuff and/or the stent at a plurality of locations to form a pocket(s) between the first and second cuffs. The proximal edge of the second cuff may be coupled to first cuff and/or to the stent at a spaced distance from the inflow end of the stent.

18 Claims, 9 Drawing Sheets

(56) References Cited

U.S. PATENT DOCUMENTS

| | | |
|---|---|---|
| 4,491,986 A | 1/1985 | Gabbay |
| 4,759,758 A | 7/1988 | Gabbay |
| 4,878,906 A | 11/1989 | Lindemann et al. |
| 4,922,905 A | 5/1990 | Strecker |
| 4,994,077 A | 2/1991 | Dobben |
| 5,411,552 A | 5/1995 | Andersen et al. |
| 5,415,664 A | 5/1995 | Pinchuk |
| 5,480,423 A | 1/1996 | Ravenscroft et al. |
| 5,843,167 A | 12/1998 | Dwyer et al. |
| 5,855,601 A | 1/1999 | Bessler et al. |
| 5,935,163 A | 8/1999 | Gabbay |
| 5,961,549 A | 10/1999 | Nguyen et al. |
| 6,045,576 A | 4/2000 | Starr et al. |
| 6,077,297 A | 6/2000 | Robinson et al. |
| 6,083,257 A | 7/2000 | Taylor et al. |
| 6,090,140 A | 7/2000 | Gabbay |
| 6,214,036 B1 | 4/2001 | Letendre et al. |
| 6,264,691 B1 | 7/2001 | Gabbay |
| 6,267,783 B1 | 7/2001 | Letendre et al. |
| 6,368,348 B1 | 4/2002 | Gabbay |
| 6,419,695 B1 | 7/2002 | Gabbay |
| 6,458,153 B1 | 10/2002 | Bailey et al. |
| 6,468,660 B2 | 10/2002 | Ogle et al. |
| 6,488,702 B1 | 12/2002 | Besselink |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,623,518 B2 | 9/2003 | Thompson et al. |
| 6,652,578 B2 | 11/2003 | Bailey et al. |
| 6,685,625 B2 | 2/2004 | Gabbay |
| 6,716,244 B2 | 4/2004 | Klaco |
| 6,719,789 B2 | 4/2004 | Cox |
| 6,730,118 B2 | 5/2004 | Spenser et al. |
| 6,783,556 B1 | 8/2004 | Gabbay |
| 6,790,230 B2 | 9/2004 | Beyersdorf et al. |
| 6,814,746 B2 | 11/2004 | Thompson et al. |
| 6,830,584 B1 | 12/2004 | Seguin |
| 6,869,444 B2 | 3/2005 | Gabbay |
| 6,893,460 B2 | 5/2005 | Spenser et al. |
| 6,908,481 B2 | 6/2005 | Cribier |
| 6,951,573 B1 | 10/2005 | Dilling |
| 7,018,406 B2 | 3/2006 | Seguin et al. |
| 7,025,780 B2 | 4/2006 | Gabbay |
| 7,137,184 B2 | 11/2006 | Schreck |
| 7,160,322 B2 | 1/2007 | Gabbay |
| 7,195,641 B2 | 3/2007 | Palmaz et al. |
| 7,247,167 B2 | 7/2007 | Gabbay |
| 7,267,686 B2 | 9/2007 | DiMatteo et al. |
| 7,276,078 B2 | 10/2007 | Spenser et al. |
| 7,311,730 B2 | 12/2007 | Gabbay |
| 7,320,704 B2 | 1/2008 | Lashinski et al. |
| 7,329,278 B2 | 2/2008 | Seguin et al. |
| 7,374,573 B2 | 5/2008 | Gabbay |
| 7,381,218 B2 | 6/2008 | Schreck |
| 7,381,219 B2 | 6/2008 | Salahieh et al. |
| 7,452,371 B2 | 11/2008 | Pavcnik et al. |
| 7,510,572 B2 | 3/2009 | Gabbay |
| 7,510,575 B2 | 3/2009 | Spenser et al. |
| 7,524,331 B2 | 4/2009 | Birdsall |
| 7,534,261 B2 | 5/2009 | Friedman |
| RE40,816 E | 6/2009 | Taylor et al. |
| 7,585,321 B2 | 9/2009 | Cribier |
| 7,628,805 B2 | 12/2009 | Spenser et al. |
| 7,682,390 B2 | 3/2010 | Seguin |
| 7,708,775 B2 | 5/2010 | Rowe et al. |
| 7,731,742 B2 | 6/2010 | Schlick et al. |
| 7,748,389 B2 | 7/2010 | Salahieh et al. |
| 7,780,725 B2 | 8/2010 | Haug et al. |
| 7,799,069 B2 | 9/2010 | Bailey et al. |
| 7,803,185 B2 | 9/2010 | Gabbay |
| 7,824,442 B2 | 11/2010 | Salahieh et al. |
| 7,837,727 B2 | 11/2010 | Goetz et al. |
| 7,846,203 B2 | 12/2010 | Cribier |
| 7,846,204 B2 | 12/2010 | Letac et al. |
| 7,857,845 B2 | 12/2010 | Stacchino et al. |
| 7,892,281 B2 | 2/2011 | Seguin et al. |
| 7,914,569 B2 | 3/2011 | Nguyen et al. |
| 7,959,666 B2 | 6/2011 | Salahieh et al. |
| 7,959,672 B2 | 6/2011 | Salahieh et al. |
| 7,972,378 B2 | 7/2011 | Tabor et al. |
| 7,988,724 B2 | 8/2011 | Salahieh et al. |
| 7,993,394 B2 | 8/2011 | Hariton et al. |
| 8,016,877 B2 | 9/2011 | Seguin et al. |
| D648,854 S | 11/2011 | Braido |
| 8,048,153 B2 | 11/2011 | Salahieh et al. |
| 8,052,741 B2 | 11/2011 | Bruszewski et al. |
| 8,052,749 B2 | 11/2011 | Salahieh et al. |
| 8,052,750 B2 | 11/2011 | Tuval et al. |
| 8,062,355 B2 | 11/2011 | Figulla et al. |
| 8,075,611 B2 | 12/2011 | Millwee et al. |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| 8,137,398 B2 | 3/2012 | Tuval et al. |
| 8,142,497 B2 | 3/2012 | Friedman |
| D660,432 S | 5/2012 | Braido |
| D660,433 S | 5/2012 | Braido et al. |
| D660,967 S | 5/2012 | Braido et al. |
| 8,182,528 B2 | 5/2012 | Salahieh et al. |
| 8,221,493 B2 | 7/2012 | Boyle et al. |
| 8,230,717 B2 | 7/2012 | Matonick |
| 8,231,670 B2 | 7/2012 | Salahieh et al. |
| 8,252,051 B2 | 8/2012 | Chau et al. |
| 8,308,798 B2 | 11/2012 | Pintor et al. |
| 8,313,525 B2 | 11/2012 | Tuval et al. |
| 8,323,335 B2 | 12/2012 | Rowe et al. |
| 8,323,336 B2 | 12/2012 | Hill et al. |
| 8,343,213 B2 | 1/2013 | Salahieh et al. |
| 8,348,995 B2 | 1/2013 | Tuval et al. |
| 8,348,996 B2 | 1/2013 | Tuval et al. |
| 8,348,998 B2 | 1/2013 | Pintor et al. |
| 8,366,769 B2 | 2/2013 | Huynh et al. |
| 8,403,983 B2 | 3/2013 | Quadri et al. |
| 8,408,214 B2 | 4/2013 | Spenser |
| 8,414,643 B2 | 4/2013 | Tuval et al. |
| 8,425,593 B2 | 4/2013 | Braido et al. |
| 8,449,599 B2 | 5/2013 | Chau et al. |
| 8,449,604 B2 | 5/2013 | Moaddeb et al. |
| D684,692 S | 6/2013 | Braido |
| 8,454,686 B2 | 6/2013 | Alkhatib |
| 8,500,798 B2 | 8/2013 | Rowe et al. |
| 8,568,474 B2 | 10/2013 | Yeung et al. |
| 8,579,962 B2 | 11/2013 | Salahieh et al. |
| 8,579,966 B2 | 11/2013 | Seguin et al. |
| 8,585,755 B2 | 11/2013 | Chau et al. |
| 8,591,575 B2 | 11/2013 | Cribier |
| 8,597,349 B2 | 12/2013 | Alkhatib |
| 8,603,159 B2 | 12/2013 | Seguin et al. |
| 8,603,160 B2 | 12/2013 | Salahieh et al. |
| 8,613,765 B2 | 12/2013 | Bonhoeffer et al. |
| 8,623,074 B2 | 1/2014 | Ryan |
| 8,652,204 B2 | 2/2014 | Quill et al. |
| 8,663,322 B2 | 3/2014 | Keranen |
| 8,668,733 B2 | 3/2014 | Haug et al. |
| 8,685,080 B2 | 4/2014 | White |
| 8,728,154 B2 | 5/2014 | Alkhatib |
| 8,747,459 B2 | 6/2014 | Nguyen et al. |
| 8,764,820 B2 | 7/2014 | Dehdashtian et al. |
| 8,795,357 B2 | 8/2014 | Yohanan et al. |
| 8,801,776 B2 | 8/2014 | House et al. |
| 8,808,356 B2 | 8/2014 | Braido et al. |
| 8,828,078 B2 | 9/2014 | Salahieh et al. |
| 8,834,563 B2 | 9/2014 | Righini |
| 8,840,661 B2 | 9/2014 | Manasse |
| 8,840,663 B2 | 9/2014 | Salahieh et al. |
| 8,876,894 B2 | 11/2014 | Tuval et al. |
| 8,876,895 B2 | 11/2014 | Tuval et al. |
| 8,940,040 B2 | 1/2015 | Shahriari |
| 8,945,209 B2 | 2/2015 | Bonyuet et al. |

(56) References Cited

U.S. PATENT DOCUMENTS

| | | |
|---|---|---|
| 8,961,595 B2 | 2/2015 | Alkhatib |
| 8,974,523 B2 | 3/2015 | Thill et al. |
| 8,974,524 B2 | 3/2015 | Yeung et al. |
| 2002/0036220 A1 | 3/2002 | Gabbay |
| 2003/0023303 A1 | 1/2003 | Palmaz et al. |
| 2003/0050694 A1 | 3/2003 | Yang et al. |
| 2003/0130726 A1 | 7/2003 | Thorpe et al. |
| 2004/0049262 A1 | 3/2004 | Obermiller et al. |
| 2004/0093075 A1 | 5/2004 | Kuehne |
| 2004/0111111 A1 | 6/2004 | Lin |
| 2004/0210304 A1 | 10/2004 | Seguin et al. |
| 2004/0260389 A1 | 12/2004 | Case et al. |
| 2005/0096726 A1 | 5/2005 | Sequin et al. |
| 2005/0137682 A1 | 6/2005 | Justino |
| 2005/0137695 A1 | 6/2005 | Salahieh et al. |
| 2005/0137697 A1 | 6/2005 | Salahieh et al. |
| 2005/0203605 A1 | 9/2005 | Dolan |
| 2005/0240200 A1 | 10/2005 | Bergheim |
| 2005/0256566 A1 | 11/2005 | Gabbay |
| 2006/0008497 A1 | 1/2006 | Gabbay |
| 2006/0074484 A1 | 4/2006 | Huber |
| 2006/0122692 A1 | 6/2006 | Gilad et al. |
| 2006/0149360 A1 | 7/2006 | Schwammenthal et al. |
| 2006/0161249 A1 | 7/2006 | Realyvasquez et al. |
| 2006/0173532 A1 | 8/2006 | Flagle et al. |
| 2006/0178740 A1 | 8/2006 | Stacchino et al. |
| 2006/0195180 A1 | 8/2006 | Kheradvar et al. |
| 2006/0206202 A1 | 9/2006 | Bonhoeffer et al. |
| 2006/0241744 A1 | 10/2006 | Beith |
| 2006/0259120 A1 | 11/2006 | Vongphakdy et al. |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2006/0276874 A1 | 12/2006 | Wilson et al. |
| 2007/0010876 A1 | 1/2007 | Salahieh et al. |
| 2007/0027534 A1 | 2/2007 | Bergheim et al. |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0093890 A1 | 4/2007 | Eliasen et al. |
| 2007/0100435 A1 | 5/2007 | Case et al. |
| 2007/0118210 A1 | 5/2007 | Pinchuk |
| 2007/0213813 A1 | 9/2007 | Von Segesser et al. |
| 2007/0233228 A1 | 10/2007 | Eberhardt et al. |
| 2007/0244545 A1 | 10/2007 | Birdsall et al. |
| 2007/0244552 A1 | 10/2007 | Salahieh et al. |
| 2007/0288087 A1 | 12/2007 | Fearnot et al. |
| 2008/0021552 A1 | 1/2008 | Gabbay |
| 2008/0039934 A1 | 2/2008 | Styrc |
| 2008/0071369 A1 | 3/2008 | Tuval et al. |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2009/0099653 A1 | 4/2009 | Suri et al. |
| 2009/0112309 A1 | 4/2009 | Jaramillo et al. |
| 2009/0138079 A1 | 5/2009 | Tuval et al. |
| 2009/0276027 A1 | 11/2009 | Glynn |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0087907 A1 | 4/2010 | Lattouf |
| 2010/0131055 A1 | 5/2010 | Case et al. |
| 2010/0168778 A1 | 7/2010 | Braido |
| 2010/0168839 A1 | 7/2010 | Braido et al. |
| 2010/0168844 A1 | 7/2010 | Toomes et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0234940 A1 | 9/2010 | Dolan |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1 | 11/2010 | Quadri et al. |
| 2011/0029072 A1 | 2/2011 | Gabbay |
| 2011/0054466 A1 | 3/2011 | Rothstein et al. |
| 2011/0098800 A1 | 4/2011 | Braido et al. |
| 2011/0098802 A1 | 4/2011 | Braido et al. |
| 2011/0137397 A1 | 6/2011 | Chau et al. |
| 2011/0172765 A1 | 7/2011 | Nguyen et al. |
| 2011/0208283 A1 | 8/2011 | Rust |
| 2011/0264206 A1 | 10/2011 | Tabor |
| 2012/0035722 A1 | 2/2012 | Tuval |
| 2012/0078347 A1 | 3/2012 | Braido et al. |
| 2012/0078352 A1 | 3/2012 | Wang et al. |
| 2012/0101572 A1 | 4/2012 | Kovalsky et al. |
| 2012/0123529 A1 | 5/2012 | Levi et al. |
| 2012/0303116 A1 | 11/2012 | Gorman, III et al. |
| 2013/0274873 A1 | 10/2013 | Delaloye et al. |
| 2014/0121763 A1 | 5/2014 | Duffy et al. |
| 2014/0155997 A1 | 6/2014 | Braido |
| 2014/0214159 A1 | 7/2014 | Vidlund et al. |
| 2014/0228946 A1 | 8/2014 | Chau et al. |
| 2014/0277417 A1* | 9/2014 | Schraut ............... A61F 2/2403 623/2.17 |
| 2014/0303719 A1 | 10/2014 | Cox et al. |
| 2014/0324164 A1 | 10/2014 | Gross et al. |
| 2014/0343671 A1 | 11/2014 | Yohanan et al. |
| 2014/0350668 A1 | 11/2014 | Delaloye et al. |
| 2014/0350669 A1 | 11/2014 | Gillespie et al. |
| 2016/0250022 A1* | 9/2016 | Braido ............... A61F 2/2418 623/2.38 |
| 2018/0055631 A1 | 3/2018 | Morin et al. |

FOREIGN PATENT DOCUMENTS

| | | |
|---|---|---|
| DE | 102005003632 A1 | 8/2006 |
| DE | 202008009610 U1 | 12/2008 |
| EP | 0850607 A1 | 7/1998 |
| EP | 1000590 A1 | 5/2000 |
| EP | 1584306 A1 | 10/2005 |
| EP | 1598031 A2 | 11/2005 |
| EP | 1360942 B1 | 12/2005 |
| EP | 1926455 A2 | 6/2008 |
| EP | 2537487 A1 | 12/2012 |
| EP | 2898859 A1 | 7/2015 |
| FR | 2850008 A1 | 7/2004 |
| FR | 2847800 B1 | 10/2005 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 01028459 A1 | 4/2001 |
| WO | 2001049213 A2 | 7/2001 |
| WO | 0154625 A1 | 8/2001 |
| WO | 01056500 A2 | 8/2001 |
| WO | 0176510 A2 | 10/2001 |
| WO | 2002036048 A1 | 5/2002 |
| WO | 0247575 A2 | 6/2002 |
| WO | 02067782 A2 | 9/2002 |
| WO | 03047468 A1 | 6/2003 |
| WO | 2005070343 A1 | 8/2005 |
| WO | 06073626 A2 | 7/2006 |
| WO | 07071436 A2 | 6/2007 |
| WO | 08070797 A2 | 6/2008 |
| WO | 10008548 A2 | 1/2010 |
| WO | 2010008549 A1 | 1/2010 |
| WO | 2010096176 A1 | 8/2010 |

(56) References Cited

FOREIGN PATENT DOCUMENTS

| WO | 2010098857 A1 | 9/2010 |
|---|---|---|
| WO | 2015175524 A1 | 11/2015 |

OTHER PUBLICATIONS

"Closed Heart Surgery: Back to the Future", Samuel V. Lichtenstein, The Journal of Thoracic and Cardiovascular Surgery, vol. 131, No. 5, May 2006, pp. 941-943.
"Direct-Access Valve Replacement", Christoph H. Huber, et al., Journal of the American College of Cardiology, vol. 46, No. 2, (Jul. 19, 2005).
"Minimally invasive cardiac surgery", M. J. Mack, Surgical Endoscopy, 2006, 20:S488-S492, DOI: 10.1007/s00464-006-0110-8 (presented Mar. 23, 2006).
"Percutaneous Aortic Valve Implantation Retrograde From the Femoral Artery", John G. Webb et al., Circulation, 2006; 113:842-850 (Feb. 6, 2006).
"Percutaneous Aortic Valve Replacement: Resection Before Implantation", Quaden, Rene et al., European J. of Cardio-Thoracic Surgery, vol. 27, No. 5, May 2005, pp. 836-840.
"Transapical aortic valve implantation: an animal feasibility study"; Todd M. Dewey et al., The annals of thoracic surgery 2006; 82:110-6 (Feb. 13, 2006).
"Transapical Approach for Sutureless Stent-Fixed Aortic Valve Implantation: Experimental Results", Th. Walther et al., European Journal of Cardio-Thoracic Surgery, vol. 29, No. 5, May 2006, pp. 703-708.
"Transapical Transcatheter Aortic Valve Implantation in Humans", Samuel V. Lichtenstein et al., Circulation. 2006; 114:591-596 (Jul. 31, 2006).
"Transcatheter Umbrella Closure of Valvular and Paravalvular Leaks", Hourihan et al., Journal of the American College of Cardiology, vol. 20, No. 6, Nov. 1992, pp. 1371-1377.
"Transluminal Aortic Valve Placement. A Feasability Study with a Newly Designed Collapsible Aortic Valve", Moazami et al., ASAIO Journal, vol. 42, No. 5, 1996, pp. M381-M385.
"Transluminal Catheter Implanted Prosthetic Heart Valves", Andersen, H. R., International Journal of Angiology, vol. 7, No. 2, Mar. 1998, pp. 102-106.
"Transluminal Implantation of Artificial Heart Valves", Andersen, H. R., et al., European Heart Journal, vol. 13, No. 5, May 1992, pp. 704-708.
Buellesfeld et al., "Treatment of Paravalvular Leaks Through Inverventional Techniques", Multimedia Manual of Cardithoracic Surgery, Department of Cardiology, Ben University Hospital, Jan. 2011.
De Cicco, et al., "Aortic Valve Periprosthetic Leakage: Anatomic Observations and Surgical Results", The Annals of Thoracic Surgery, vol. 79, No. 5, May 2005, pp. 1480-1485.
Gössl and Rihal, "Percutaneous Treatment of Aortic and Mitral Valve Paravalvular Regurgitation", Current Cardiology Reports, vol. 15, No. 8, Aug. 2013, pp. 1-8.
Heat Advisor, "Heart repairs without surgery. Minimally invasive procedures aim to correct valve leakage", Sep. 2004, PubMed ID 15586429.
Is It Reasonable to Treat All Calcified Stenotic Aortic Valves With a Valved Stent?, 579-584, Zegdi, Rachid, MD, PhD at al., J. of the American College of Cardiology, vol. 51, No. 5, Feb. 5, 2008.
Muñoz, Daniel Rodriguez, Carla Lázaro Rivera, and José Luis Zamorano Gómez, "Guidance of Treatment of Perivalvular Prosthetic Leaks", Current Cardiology Reports, vol. 16, No. 1, Nov. 2013, pp. 1-6.
Rohde, I., Masch, J.-M., Theisen-Kunde, D., Marczynski-Bühlow, M., Bombien Quaden, R., Lutter, G. and Brinkmann, R., "Resection of Calcified Aortic Heart Leaflets In Vitro by Q-Switched 2?μm Microsecond Laser Radiation", Journal of Cardiac Surgery, vol. 30, No. 2, Feb. 2015, pp. 157-162. doi: 10.1111/jocs.12481.
Ruiz, Carlos, Overview of PRE-CE Mark Transcatheter Aortic Valve Technologies, Euro PCR, dated May 25, 2010.
Swiatkiewicz et al., "Percutaneous Closure of Mitral Perivalvular Leak", Kardiologia Polska, vol. 67, No. 7, 2009, pp. 762-764.
Transcatheter Valve Repair, Hijazi et al., CRC Press, Jan. 2006, pp. 165-186.
U.S. Appl. No. 29/375,243—Braido, et al., U.S. Appl. No. 29/375,243, filed Sep. 20, 2010, titled "Surgical Stent Assembly".
International Search Report including Written Opinion for PCT/US2019/065119 dated Mar. 3, 2020; 14 pages.

* cited by examiner

ELEVATED OUTER CUFF FOR REDUCING PARAVALVULAR LEAKAGE AND INCREASING STENT FATIGUE LIFE

CROSS-REFERENCE TO RELATED APPLICATIONS

This application claims the benefit of the filing date of U.S. Provisional Patent Application No. 62/784,923 filed Dec. 26, 2018, the disclosure of which is hereby incorporated by reference herein.

BACKGROUND OF THE DISCLOSURE

The present disclosure relates to heart valve replacement and, in particular, to collapsible prosthetic heart valves. More particularly, the present disclosure relates to collapsible prosthetic transcatheter heart valves that minimize or reduce paravalvular leaks.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two common types of stents on which the valve structures are ordinarily mounted: a self-expanding stent and a balloon-expandable stent. To load such valves into a delivery apparatus and deliver them into a patient, the valve is first collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the valve, assuring its proper location, and then expanding a balloon positioned within the valve stent. For self-expanding valves, on the other hand, the stent automatically expands as a sheath covering the valve is withdrawn.

After implantation, imperfect sealing between the prosthetic valve and the native tissue at the site of implantation may cause complications such as paravalvular leakage ("PV leak") in which retrograde blood flows through one or more gaps formed between the structure of the implanted valve and cardiac tissue as a result of the imperfect sealing.

BRIEF SUMMARY

According to one aspect of the disclosure, a prosthetic heart valve for replacing a native valve includes a stent extending in a longitudinal direction from an inflow end to an outflow end. A valve assembly may be disposed within the stent. A first cuff may be annularly disposed adjacent the stent. A second cuff may have a proximal edge facing toward the inflow end of the stent and a distal edge facing toward the outflow end of the stent. The second cuff may be annularly disposed about the stent radially outward of the first cuff. The distal edge of the second cuff may be coupled to at least one of the first cuff and the stent at a plurality of locations spaced apart in a circumferential direction of the stent to form at least one pocket between the first cuff and the second cuff. The proximal edge of the second cuff may be coupled to at least one of the first cuff and the stent at a spaced distance from the inflow end of the stent.

According to another aspect of the disclosure, a method of implanting a prosthetic heart valve into a valve annulus of a patient may include introducing the prosthetic heart valve into the valve annulus of the patient. The prosthetic heart valve may include a stent, a valve assembly disposed within the stent, a first cuff annularly disposed adjacent the stent, and a second cuff annularly disposed on an exterior of the stent radially outward of the first cuff. The method may include positioning the prosthetic heart valve in the valve annulus of the patient so that a sub-annular portion of the stent extends beyond the native valve annulus so that the sub-annular portion of the stent is not in direct contact with the native valve annulus. The sub-annular portion of the stent may include an inflow end of the stent. A portion of the second cuff may be in direct contact with the native valve annulus. The sub-annular portion of the stent may be uncovered by the second cuff.

BRIEF DESCRIPTION OF THE DRAWINGS

Various embodiments of the presently disclosed prosthetic heart valve may be more fully understood with reference to the following detailed description when read with the accompanying drawings, in which.

DETAILED DESCRIPTION

As used herein in connection with a prosthetic heart valve, the term "inflow end" refers to the end of the heart valve through which blood enters when the valve is functioning as intended, and the term "outflow end" refers to the end of the heart valve through which blood exits when the valve is functioning as intended. As used herein, the term "proximal" refers to the inflow end of a prosthetic heart valve or to elements of a prosthetic heart valve that are relatively close to the inflow end, and the term "distal" refers to the outflow end of a prosthetic heart valve or to elements of a prosthetic heart valve that are relatively close to the outflow end. As used herein, the terms "generally," "substantially," and "about" are intended to mean that slight deviations from absolute are included within the scope of the term so modified. Like numbers refer to similar or identical elements throughout. When used herein in the context of a prosthetic heart valve, or a component thereof, the lengthwise or axial direction refers to a direction parallel to a longitudinal axis passing through the center of the stent or heart valve from the inflow end to the outflow end. When used herein in the context of a prosthetic heart valve, or a component thereof, the circumferential direction refers to a direction extending along the circumference of the prosthetic heart valve.

Figure 1:
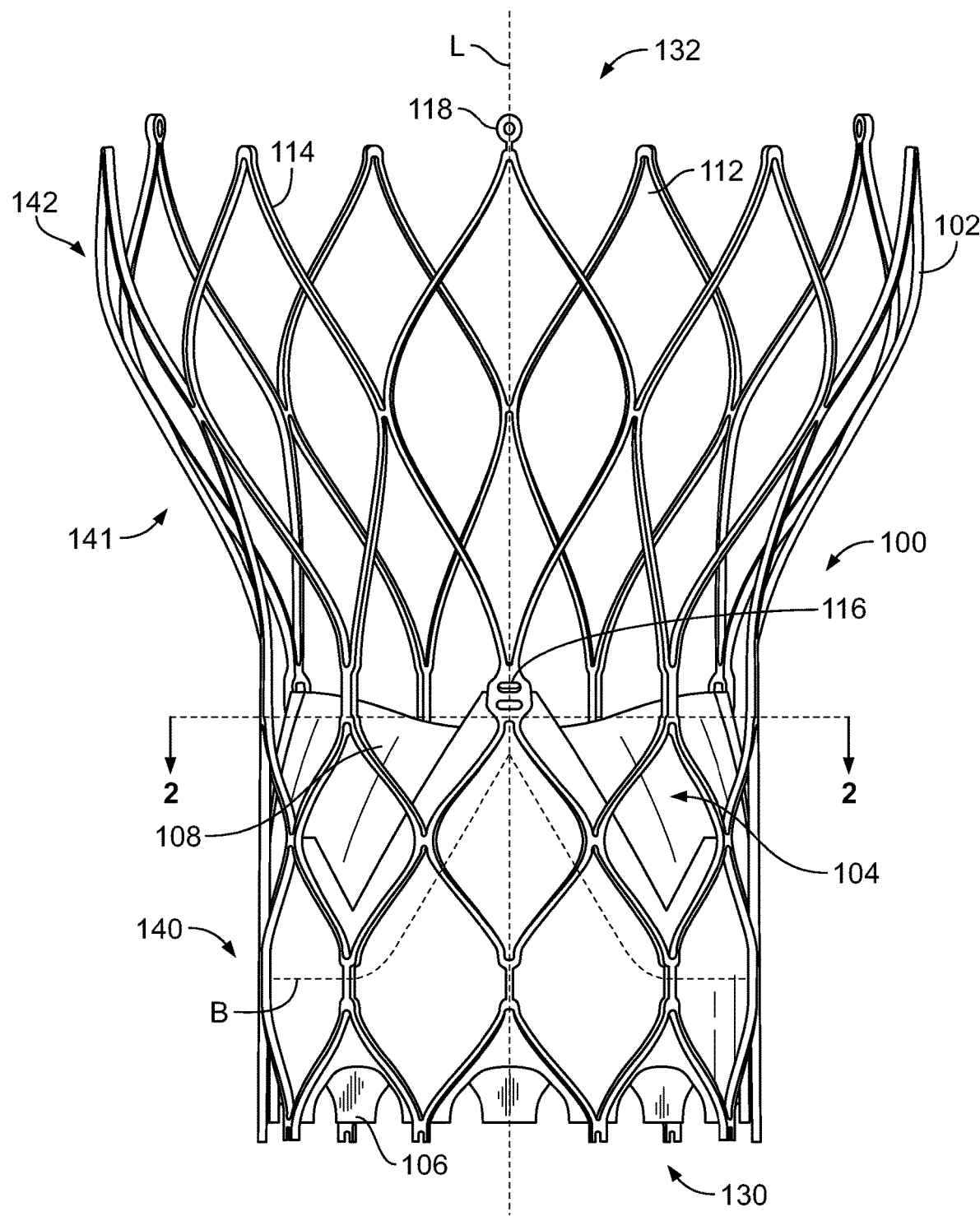
FIG. 1 is a front view of a collapsible prosthetic heart valve according to the prior art, shown in an expanded condition.

FIG. 1 shows a collapsible stent-supported prosthetic heart valve 100 according to the prior art, the prosthetic heart valve being shown in an expanded condition. Prosthetic heart valve 100 is designed to replace the function of the native aortic valve of a patient. Prosthetic heart valve 100 includes a stent 102 which serves as a frame for the valve elements. Stent 102 extends along a lengthwise or longitudinal axis L from an inflow or annulus end 130 to an outflow or aortic end 132, and includes an annulus section 140 adjacent inflow end 130 and an aortic section 142 adjacent outflow end 132. Annulus section 140 may be in the form of a cylinder having a substantially constant diameter along its length, and may have a relatively small transverse cross-section in the expanded condition in comparison to the transverse cross-section of aortic section 142. A transition section 141 may taper outwardly from annulus section 140 to aortic section 142. Each of the sections of stent 102 includes a plurality of cells 112 formed by interconnected struts 114. Each cell 112 may include four struts 114 connected together generally in a diamond shape so as to form a cell that may be readily collapsed and expanded. It will be appreciated that a smaller or larger number of struts may be used to form cells having a different shape. The cells 112 in each section of stent 102 may be connected to one another in one or more annular rows around the stent. For example, as shown in FIG. 1, annulus section 140 may have two annular rows of complete cells 112, with the cells in one annular row offset by one-half cell width in the circumferential direction from the cells in the other annular row. Aortic section 142 and transition section 141 may each have one or more annular rows of complete or partial cells 112. The cells in aortic section 142 may be larger than the cells in annulus section 140 so as to better enable prosthetic valve 100 to be positioned within the aortic annulus without the structure of stent 102 interfering with blood flow to the coronary arteries. At least partly due to the shape of cells 112, stent 102 elongates in the direction of longitudinal axis L as the cells collapse when the stent transitions from the expanded condition to the collapsed condition, and shortens in the direction of longitudinal axis L as the stent transitions from the collapsed condition to the expanded condition.

Stent 102 may include one or more retaining elements 118 at outflow end 132, the retaining elements being sized and shaped to cooperate with retaining structures provided on a deployment device (not shown). The engagement of retaining elements 118 with the retaining structures on the deployment device may help maintain prosthetic heart valve 100 in assembled relationship with the deployment device, minimize longitudinal movement of the prosthetic heart valve relative to the deployment device during unsheathing or resheathing procedures, and help prevent rotation of the prosthetic heart valve relative to the deployment device as the deployment device is advanced to the target location and during deployment. One such deployment device is described in U.S. Patent Publication No. 2012/0078352, the entire contents of which are hereby incorporated by reference herein.

Stent 102 may also include a plurality of commissure attachment features 116 for mounting the commissures of the valve assembly to the stent. As can be seen in FIG. 1, each commissure attachment feature 116 may lie at the intersection of four cells 112, two of the cells being adjacent one another in the same annular row, and the other two cells being in different annular rows and lying in end-to-end relationship. Commissure attachment features 116 may be positioned entirely within annulus section 140 or at the juncture of annulus section 140 and transition section 141, and may include one or more eyelets or apertures which facilitate the suturing of the leaflet commissures to stent 102. Stent 102 may be formed as a unitary structure, for example, by laser cutting or etching a tube of a superelastic and/or shape-memory metal alloy, such as a nickel-titanium alloy of the type sold under the designation nitinol. Such a unitary structure may be referred to as a "non-woven" structure in that it is not formed by weaving or winding one or more filaments.

Prosthetic heart valve 100 includes a valve assembly 104 positioned in the annulus section 140 of stent 102. Valve assembly 104 includes a plurality of leaflets 108 that collectively function as a one way valve by coapting with one another, and a cuff 106 positioned on the luminal surface of stent 102 surrounding leaflets 108. As prosthetic heart valve 100 is intended to replace the aortic valve (which ordinarily is a tri-leaflet valve), it is shown in FIG. 1 with three leaflets 108. Adjacent leaflets 108 join one another at leaflet commissures. Each of the leaflet commissures may be sutured to a respective one of the three commissure attachment features 116. Between the leaflet commissures, each leaflet 108 may be sutured to stent 102 and/or to cuff 106 along a leaflet belly B, indicated with broken lines in FIG. 1. Leaflets 108 may be joined to stent 102 and/or to cuff 106 by techniques known in the art other than suturing. Above belly B, leaflets 108 are free to move radially inward to coapt with one another along their free edges. When prosthetic heart valve 100 is implanted in the native aortic valve annulus, blood flows in an antegrade direction from inflow end 130, past leaflets 108, and toward outflow end 132. This occurs when the pressure in the left ventricle is greater than the pressure in the aorta, forcing leaflets 108 to open. When the pressure in the aorta is greater than the pressure in the left ventricle, leaflets 108 are forced closed and coapt with one another along their free edges, blocking blood from flowing through prosthetic heart valve 100 in a retrograde direction from outflow end 132 to inflow end 130. It will be appreciated that prosthetic heart valves according to aspects of the present disclosure may have more or less than the three leaflets 108 and commissure attachment features 116 shown in FIG. 1 and described above.

Although cuff 106 is shown in FIG. 1 as being disposed on the luminal or inner surface of annulus section 140, the cuff may be disposed on the abluminal or outer surface of the annulus section, or may cover all or part of either or both of the luminal and abluminal surfaces of the annulus section. Cuff 106 may be scalloped at the inflow end 130 of stent 102, and may have a zig-zag structure at its outflow end, following certain stent struts 114 up to commissure attachment features 116 and other stent struts closer to the inflow end of the stent at circumferential positions between the commissure attachment features. As is shown in FIG. 1, in one example, the entirety of valve assembly 104, including the leaflet commissures, is positioned in the annulus section 140 of stent 102. When open, leaflets 108 may remain substantially completely within annulus section 140, or they may be designed to extend into transition section 141. In the embodiment shown, substantially the entirety of valve assembly 104 is positioned between the inflow end 130 of stent 102 and commissure attachment features 116, and none of the valve assembly is positioned between the commissure attachment features and the outflow end 132 of the stent.

In operation, prosthetic heart valve 100 described above may be used to replace a native heart valve, such as the aortic valve; a surgical heart valve; or a heart valve that has undergone a surgical procedure. Prosthetic heart valve 100 may be delivered to the desired site (e.g., near the native aortic annulus) using any suitable delivery device. During delivery, prosthetic heart valve 100 is disposed inside the delivery device in the collapsed condition. The delivery device may be introduced into the patient using any known percutaneous procedure, such as a transfemoral, transapical, or transseptal delivery procedure. Once the delivery device has reached the target site, the user may deploy prosthetic heart valve 100. Upon deployment, prosthetic heart valve 100 expands into secure engagement within the native aortic annulus. When prosthetic heart valve 100 is properly positioned inside the heart, it works as a one-way valve, allowing blood to flow in one direction and preventing blood from flowing in the opposite direction.

Figure 2:
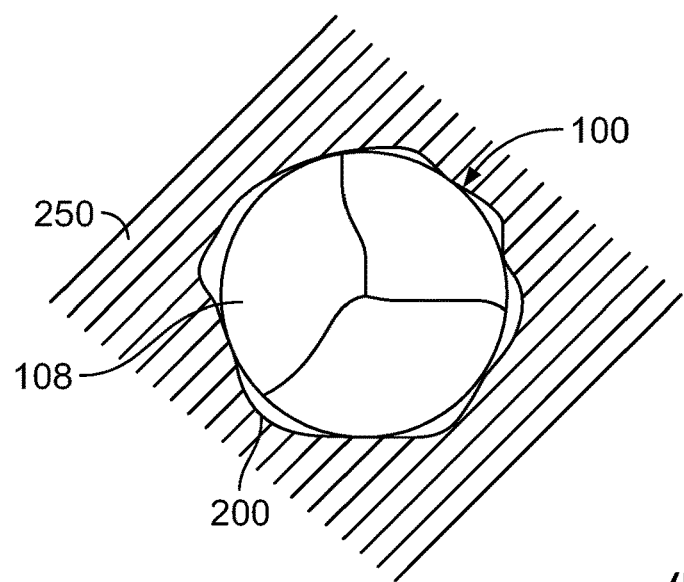
FIG. 2 is a highly schematic transverse cross-sectional view of the prior art prosthetic heart valve taken along line 2-2 of FIG. 1 and implanted in a patient.

FIG. 2 is a highly schematic transverse cross-sectional illustration taken along line 2-2 of FIG. 2 and showing prosthetic heart valve 100 with leaflets 108 disposed within native valve annulus 250. As can be seen, the substantially circular annulus section 140 of stent 102 is disposed within a non-circular native valve annulus 250. At certain locations around the perimeter of prosthetic heart valve 100, gaps 200 are formed between the heart valve and native valve annulus 250. Retrograde blood flow through these gaps and around the outside of the valve assembly 104 of prosthetic heart valve 100 can result in PV leak or regurgitation and other inefficiencies which can reduce cardiac performance. Such improper fitment may be due to suboptimal native valve annulus geometry, for example, as a result of the calcification of the tissue of native valve annulus 250 or the presence of unresected native leaflets.

Figure 3A:
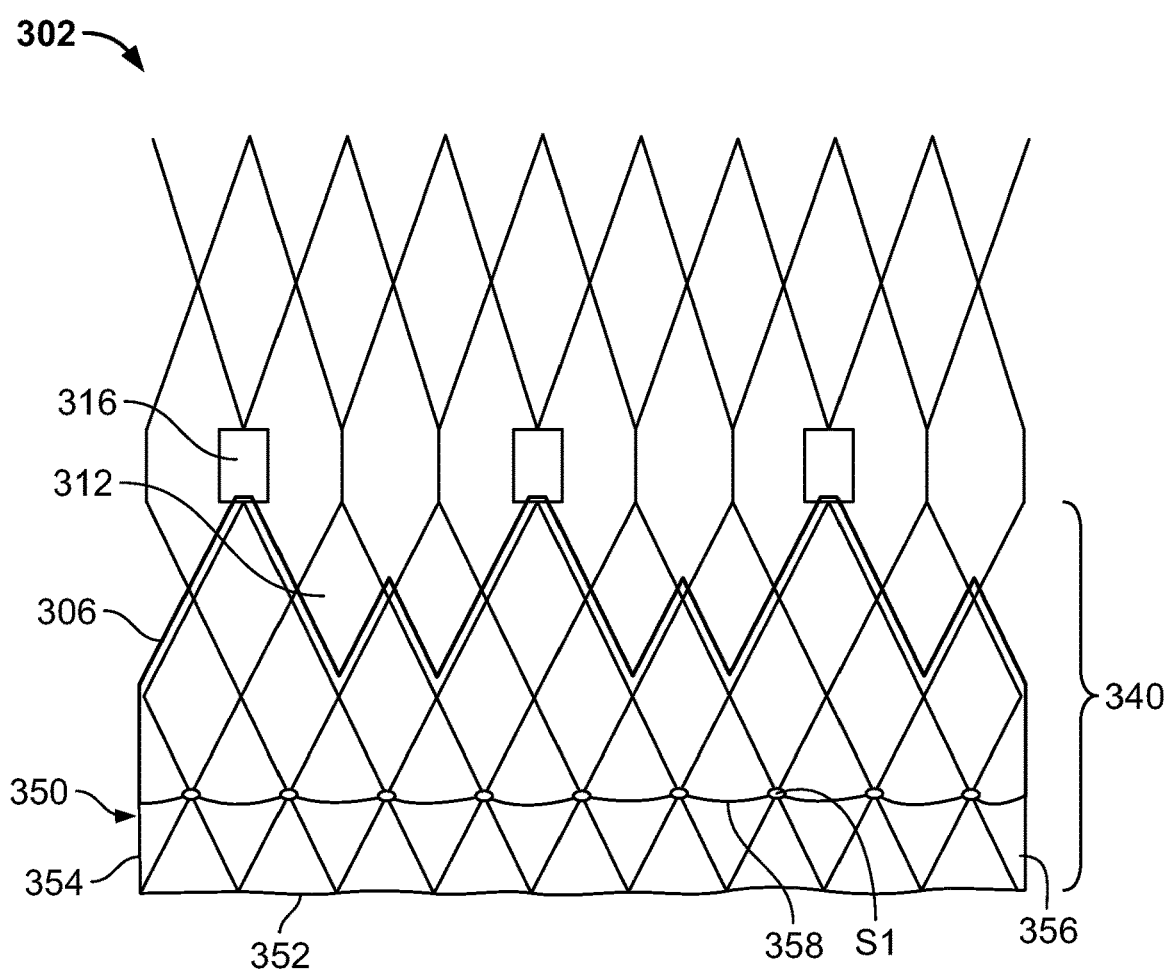
FIG. 3A is a schematic developed view of a stent with an outer cuff in an expanded condition according to an embodiment of the disclosure.
Figure 3B:
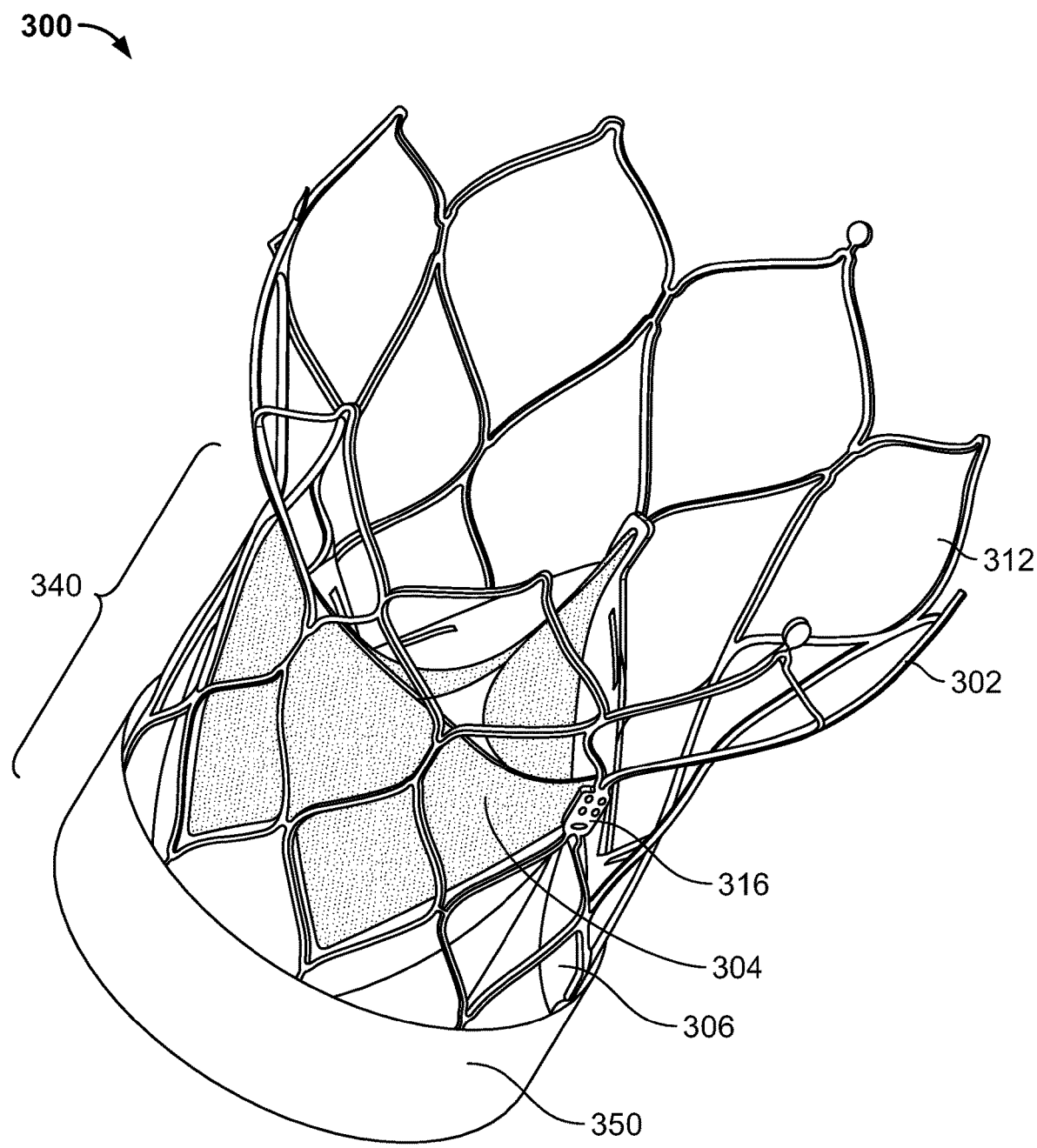
FIG. 3B is a perspective view of a prosthetic heart valve having the stent and outer cuff of FIG. 3A.

FIG. 3A illustrates the stent 302 of a prosthetic heart valve according to an aspect of the disclosure. FIG. 3B illustrates a prosthetic heart valve 300 that includes the stent 302 of FIG. 3A. Stent 302 may be similar or identical to stent 102 described above, with certain exceptions. For example, the annulus section 340 of stent 302 may include three rows of cells 312 instead of two rows, although in some embodiments stent 302 may include only two rows of cells in the annulus section, or any other number of rows of cells. Although commissure attachment features 316 of stent 302 are illustrated schematically as open rectangles in FIG. 3A, the commissure attachment features may have a form similar to commissure attachment features 116 shown in FIG. 1, or any other suitable form having any number of rows or columns of eyelets and/or eyelets of different sizes and/or shapes positioned in any arrangement on the commissure attachment feature. For example, as shown in FIG. 3B, commissure attachment features 316 may include a single elongated eyelet extending in a circumferential direction on a proximal end portion of the commissure attachment feature, with two rows and two columns of substantially rectangular-shaped eyelets positioned distally of the elongated eyelet. A cuff 306 similar or identical to cuff 106 may be positioned on the luminal and/or abluminal surface of stent 302. Rather than a scalloped inflow end as with cuff 106, however, cuff 306 may have a straight inflow end. As shown in FIG. 3B, prosthetic heart valve 300 may include a valve assembly 304 having a plurality of leaflets, similar or identical to those of valve assembly 104, positioned radially inwardly of cuff 306 and attached to that cuff.

In order to help minimize or eliminate PV leak, for example through the gaps 200 shown in FIG. 2, additional material may be coupled to the exterior of stent 302 as an outer cuff 350. In the illustrated example, outer cuff 350 may have a substantially rectangular shape and may be wrapped around the circumference of stent 302 at the inflow end of the stent so as to overlap in the longitudinal direction of the stent with cuff 306. Outer cuff 350 may be a single piece of material having a proximal edge 352, two side edges 354, 356, and a distal edge 358. Preferably, the proximal edge 352 of outer cuff 350 is coupled to stent 302 and/or to inner cuff 306 at or near the inflow end of the stent, for example by a continuous line of sutures (not shown), with the side edges 354 and 356 of the outer cuff joined to one another so that retrograde blood flow entering the space between the outer cuff and the inner cuff cannot pass in the retrograde direction beyond the combined cuffs. In order to allow retrograde blood flow to enter the space between outer cuff 350 and inner cuff 306, the distal edge 358 of the outer cuff may be attached to stent 302 and/or to inner cuff 306 at locations that are spaced apart in the circumferential direction. The distal edge 358 of outer cuff 350 may, for example, be sutured to stent 302 at attachment points S1 located where each cell 312 in the proximalmost row of cells intersects with an adjacent cell in that same row. In the illustrated example, since there are nine cells 312 in the proximalmost row, there are nine separate attachment points S1 at which the distal edge 358 of outer cuff 350 is sutured or otherwise attached to stent 302. Retrograde blood flow around the abluminal surface of stent 302 may enter the pocket or space between outer cuff 350 and inner cuff 306 via the spaces between adjacent attachment points S1. Once retrograde blood flow enters this space, outer cuff 350 may tend to billow outwardly, helping to fill any of gaps 200 between the prosthetic heart valve and native valve annulus 250. Although the foregoing description uses the term "inner" in connection with cuff 306, that is merely intended to indicate that cuff 306 is positioned radially inward of outer cuff 350. Inner cuff 306 may be located either on the luminal or abluminal side of stent 302, or on both sides.

Although described as a single piece of material above, outer cuff 350 may comprise multiple pieces of material that, when joined together, form a similar shape and provide similar function as described above for the outer cuff. Also, rather than being formed of a single substantially rectangular piece of material that is wrapped around the circumference of stent 302, outer cuff 350 may be formed as a continuous annular web without side edges 354, 356. Preferably, outer cuff 350 has an axial height measured from its proximal edge 352 to its distal edge 358 that is approximately half the axial height of a cell 312 in the proximalmost row of cells in stent 302 as measured along the major axis of the cell between two of its apices when the cell is in an expanded condition. However, outer cuff 350 may have other suitable heights, such as the full axial height of a cell 312 in the proximalmost row of cells, or more or less than the full axial height of a cell 312 in the proximalmost row of cells. Still further, although inner cuff 306 and outer cuff 350 are described above as separate pieces of material joined to stent 302 and to each other, the cuffs may be formed integrally with one another from a single piece of material that is wrapped around the proximal edge of the stent, with the distal edge 358 of the outer portion of the cuff joined to the stent and/or to the inner portion of the cuff at attachment points S1 as described above. With this configuration, the proximal edge 352 of outer cuff 350 does not need to be sutured to stent 302, although it still may be preferable to provide such attachment. Inner cuff 306 and outer cuff 350 may be formed of the same or different materials, including any suitable biological material or polymer such as, for example, polytetrafluoroethylene (PTFE), ultra-high molecular weight polyethylene (UHMWPE), polyurethane, polyvinyl alcohol, silicone, or combinations thereof.

In operation, prosthetic heart valve 300 may be transitioned into a collapsed condition and loaded onto a delivery device for delivery into a patient. Prosthetic heart valve 300 may be advanced to the aortic valve of the patient while it is maintained in the collapsed condition, for example by an overlying sheath of the delivery device that radially constrains the prosthetic heart valve. Once at the desired location, such as the native aortic valve, the overlying sheath may be removed from prosthetic heart valve 300, removing the constraining force. In the absence of any constraining forces, prosthetic heart valve 300 returns to the expanded condition. During normal operation, if any blood flows in the retrograde direction around the outside of stent 302, that blood may flow into the space between outer cuff 350 and inner cuff 306. Blood flowing into the space between inner cuff 306 and outer cuff 350 may result in the outer cuff billowing outwardly to some degree to further seal any remaining spaces between prosthetic heart valve 300 and the native aortic valve annulus, helping to mitigate or eliminate PV leak.

Figure 4:
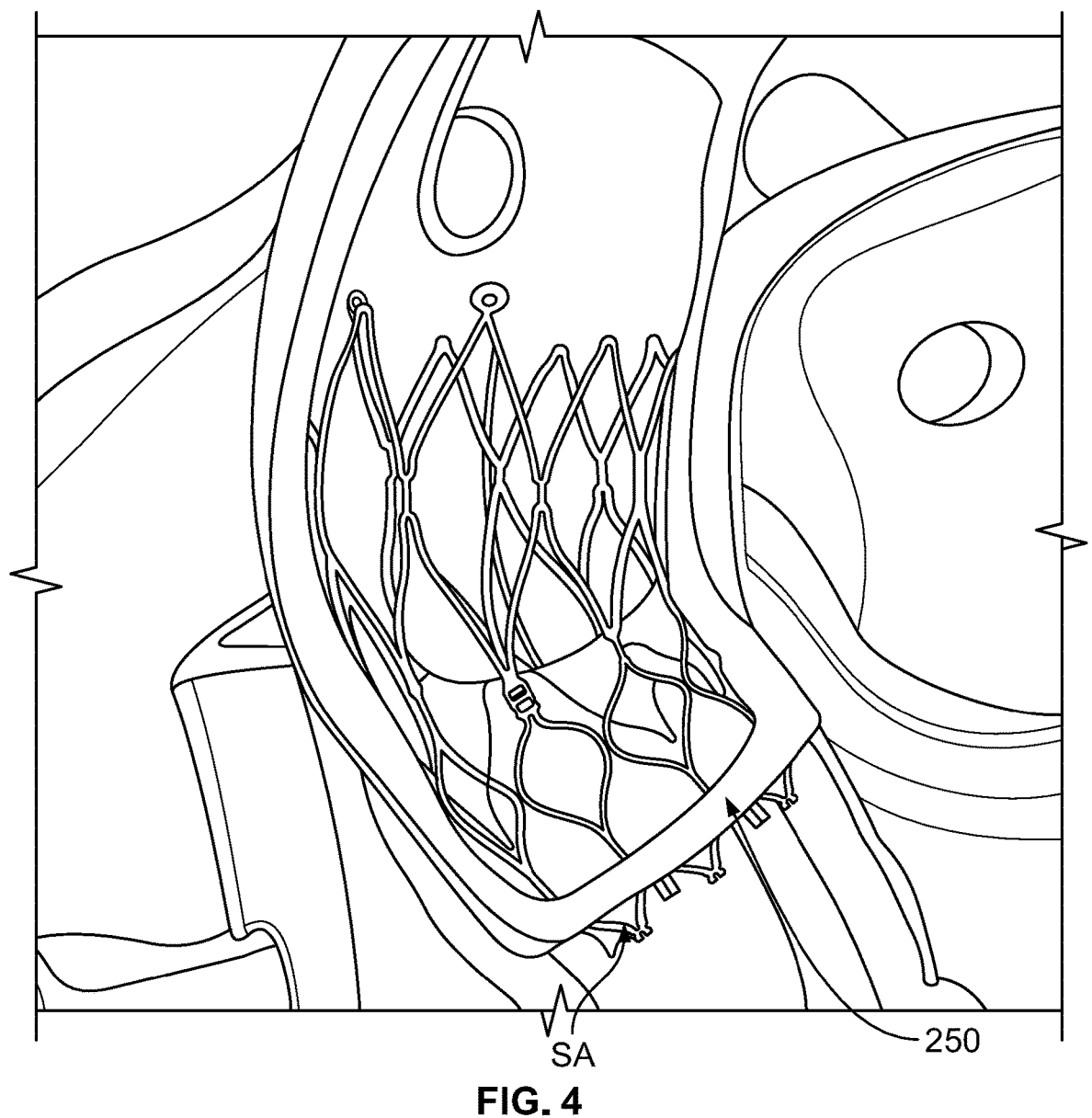
FIG. 4 is a cutaway schematic view of a prosthetic heart valve implanted in a native aortic valve.

FIG. 4 illustrates a prosthetic heart valve, for example prosthetic heart valve 100 or prosthetic heart valve 300, implanted in the native valve annulus 250 of an aortic valve. As shown in FIG. 4, the inflow end of the prosthetic heart valve is typically positioned between about 3 mm and about 6 mm below native valve annulus 250. In other words, when the prosthetic heart valve replaces the function of a native aortic valve, the prosthetic heart valve will typically have a sub-annular portion SA that includes about 3 mm to about 6 mm of structure that extends beyond native valve annulus 250 in a direction toward the left ventricle. It may be desirable to have sub-annular portion SA extend a distance beyond native valve annulus 250 to help assure full contact around the entire annulus section of the stent. For prosthetic heart valve 100, which does not include a second outer cuff as described in connection with prosthetic heart valve 300, the sub-annular portion SA may not pose any particular problems with the operation of the prosthetic heart valve. However, for prosthetic heart valve 300, the sub-annular portion SA may cause certain undesirable results in the functioning of the prosthetic heart valve. As described above, outer cuff 350 may tend to at least partially fill with blood and billow outwardly to help prevent PV leak. However, as blood flows into the space between outer cuff 350 and inner cuff 306, that blood flow may apply pressure to the inner cuff in a direction radially inwardly toward the center longitudinal axis of prosthetic heart valve 300. Because sub-annular portion SA is at the terminal (inflow) end of the stent, the portions of inner cuff 306 and stent 302 that are within the sub-annular portion of prosthetic heart valve 300 are essentially cantilevered. Thus, when retrograde blood flow enters between outer cuff 350 and inner cuff 306 and applies pressure in a radially inward direction on the inner cuff, the portion of sub-annular portion SA closest to the terminal (inflow) end of the stent is subject to the largest moment. Thus, the terminal end of the stent will tend to deflect inwardly more than portions of the stent farther away from the terminal end of the stent. The inward deflection of the sub-annular portion SA of stent 302 creates an additional mode of loading which may contribute to concerns of stent fatigue. It should be understood that prosthetic heart valves of a particular design are often provided in various sizes to account for the natural variations in size of patients' native heart valves. Given two prosthetic heart valves having the same design as prosthetic heart valve 300, with the exception that one of the prosthetic heart valves is larger than the other, the relatively large prosthetic valve may experience greater deflection in the sub-annular portion SA of the prosthetic heart valve due to this additional mode of loading, which may result in a greater concern of stent fatigue compared to the relatively small prosthetic valve.

Figure 5A:
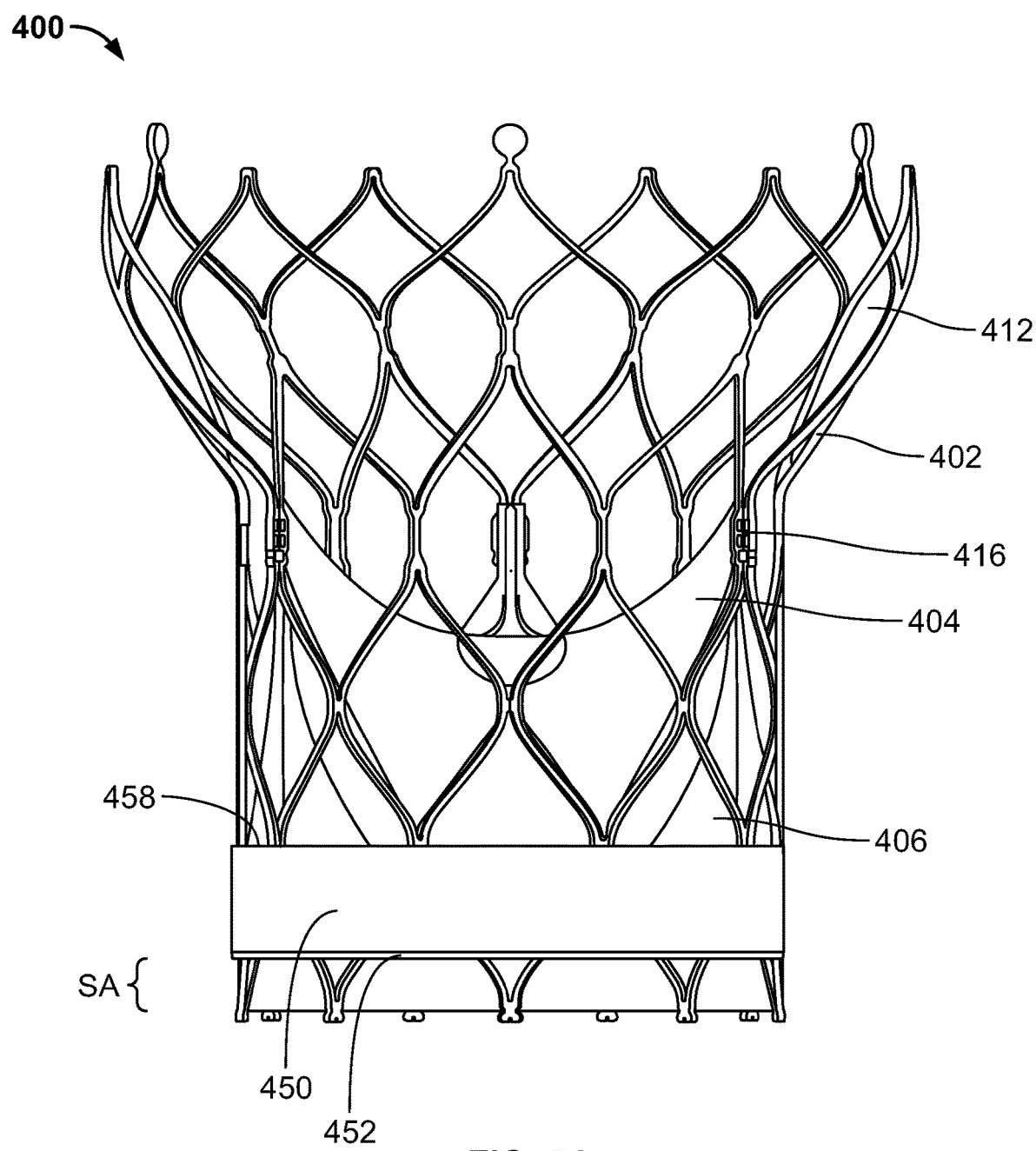
FIG. 5A is a schematic front view of a collapsible prosthetic heart valve according to another aspect of the disclosure.
Figure 5B:
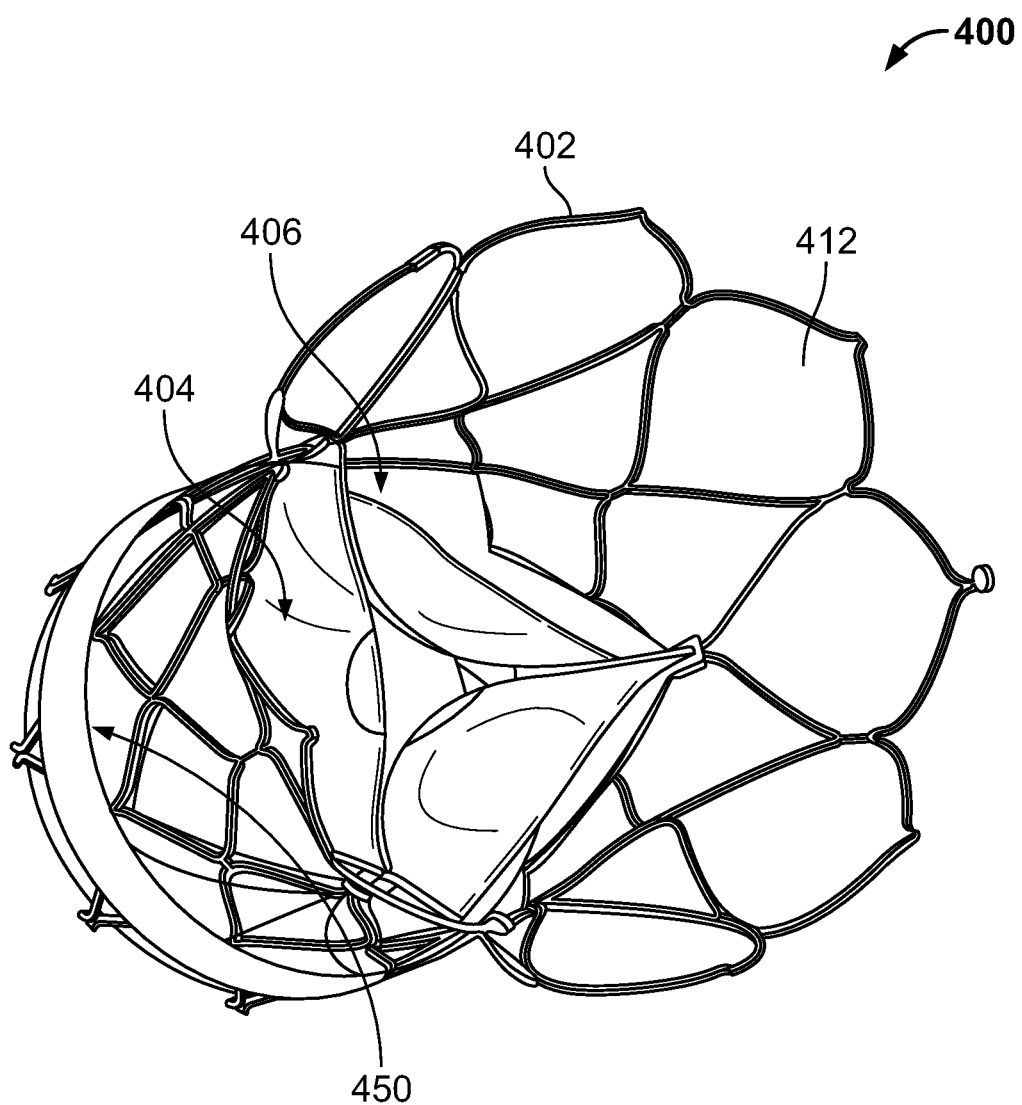
FIG. 5B is a schematic perspective view of the prosthetic heart valve of FIG. 5A.

In order to reduce the concern of additional stent fatigue due to blood flowing in the retrograde direction into the space between outer cuff 350 and inner cuff 306, without changing the positioning of prosthetic heart valve 300 relative to native valve annulus 250, the outer cuff may be provided in a modified or elevated position relative to stent 302. FIGS. 5A-B illustrate a prosthetic heart valve 400 according to an embodiment of the disclosure which may be identical or substantially identical to prosthetic heart valve 300, with the exception that outer cuff 450 is positioned farther from the inflow end of stent 402 compared to the positioning of outer cuff 350 with respect to the inflow end of stent 302. Prosthetic heart valve 400 may include a stent 402 forming a plurality of cells 412, and may include a valve assembly 404 including a plurality of leaflets attached to the stent at commissure attachment features 416, an inner cuff 406, and an outer cuff 450. It should be understood that, with the exception of outer cuff 450, the remaining components of prosthetic heart valve 400 may be identical to the corresponding components of prosthetic heart valve 300 described above and are not described in any further detail herein.

Although the position of outer cuff 450 relative to the remainder of prosthetic heart valve 400 is different than the position of outer cuff 350 relative to the remainder of prosthetic heart valve 300, the outer cuffs themselves may otherwise be substantially the same. For example, outer cuff 450 may have a substantially rectangular shape and may be wrapped around the perimeter of stent 402 near the inflow end of the stent so as to overlap in the longitudinal direction of the stent with inner cuff 406. Outer cuff 450 may be a single piece of material having a proximal edge 452, a distal edge 458, and two side edges, although the side edges may be omitted if the outer cuff takes the form of a continuous wrap of material. However, as with outer cuff 350, outer cuff 450 may comprise multiple separate pieces of material that, when joined together, form a similar shape and provide similar function as shown and described herein for the outer cuff. Inner cuff 406 and outer cuff 450 may be formed of the same or different materials, including any of those described above in connection with inner cuff 306 and outer cuff 350.

Rather than coupling proximal edge 452 to stent 402 and/or inner cuff 406 at or near the inflow edge of the stent, the proximal edge of the outer cuff is coupled to the stent and/or the inner cuff at a spaced distance from the inflow end of the stent toward the outflow end of the stent. As shown in FIG. 5A, this distance may be between about 3 mm and about 5 mm from the inflow edge, which is similar but not necessarily the same as the about 3 mm to about 6 mm length of the sub-annular portion SA.

As with outer cuff 350, the proximal edge 452 of outer cuff 450 may be coupled to stent 402 and/or to inner cuff 406, for example by a continuous line of sutures, so that retrograde blood flow entering the space between the outer cuff and the inner cuff cannot pass in the retrograde direction beyond the combined cuffs. If outer cuff 450 includes side edges, those side edges may be coupled to one another prior to, during, or after coupling the outer cuff to stent 402 and/or to inner cuff 406. In order to allow retrograde blood flow to enter the space between outer cuff 450 and inner cuff 406, the distal edge 458 of the outer cuff may be attached to stent 402 and/or to inner cuff 406 at locations that are spaced apart in the circumferential direction, similar to how outer cuff 350 is described and shown in FIG. 3A as being coupled to stent 302 and/or to inner cuff 306. For example, the distal edge 458 of outer cuff 450 may be sutured to stent 402 at attachment points located where each cell 412 in the proximalmost row of cells intersects with an adjacent cell in that same row. In the illustrated example, since there are nine cells 412 in the proximalmost row, there are nine separate attachment points at which the distal edge 458 of outer cuff 450 is sutured or otherwise attached to stent 402. Comparing the outer cuff 350 of prosthetic heart valve 300 shown in FIG. 3B to the outer cuff 450 of prosthetic heart valve 400 shown in FIGS. 5A-B, it should be understood that the attachment of the distal edges of the outer cuffs to the respective stents are substantially identical in terms of positioning, with the main difference being that outer cuff 450 has a smaller dimension between its proximal edge 452 and its distal edge 458 compared to outer cuff 350. As a result, the positions of the openings to the one or more pockets formed between outer cuff 450 and inner cuff 406 when prosthetic heart valve 400 is implanted are substantially identical to the positions of the openings to the one or more pockets formed between outer cuff 350 and inner cuff 306 when prosthetic heart valve 300 is implanted. Thus, the ability for retrograde blood flow around the abluminal surface of stent 402 to enter the pocket(s) or space(s) between outer cuff 450 and inner cuff 406 is substantially unchanged compared to prosthetic heart valve 300. Further, it should be understood that the different dimensions and/or spacing of outer cuff 450 compared to inner cuff 350 need not result in a significant change in the ability of the outer cuff of prosthetic heart valve 400 to billow open to mitigate PV leak compared to the outer cuff of prosthetic heart valve 300. At least one reason for this is that the sub-annular portion SA of outer cuff 350 does not significantly contribute to sealing upon entry of blood into the space between the outer cuff and inner cuff 306 when it is positioned beyond native valve annulus 250. In other words, eliminating the sub-annular portion SA of outer cuff 350, effectively resulting in the outer cuff 450 of prosthetic heart valve 400 shown in FIGS. 5A-B, need not reduce the ability of the outer cuff to mitigate PV leak.

As noted above, the different position and/or geometry of outer cuff 450 compared to outer cuff 350 need not reduce the ability to mitigate PV leak, but there may be a significant reduction in the forces and/or moments applied on the inflow end of stent 402 in the radially inward direction from blood flowing in the retrograde direction around the abluminal surface of the stent into the space(s) between outer cuff 450 and inner cuff 406. The reason for the reduction in the forces can be seen in the force diagrams in FIGS. 6A and 7A, and the corresponding representations of the resulting stent deflections shown in FIGS. 6B and 7B.

Figure 6A:
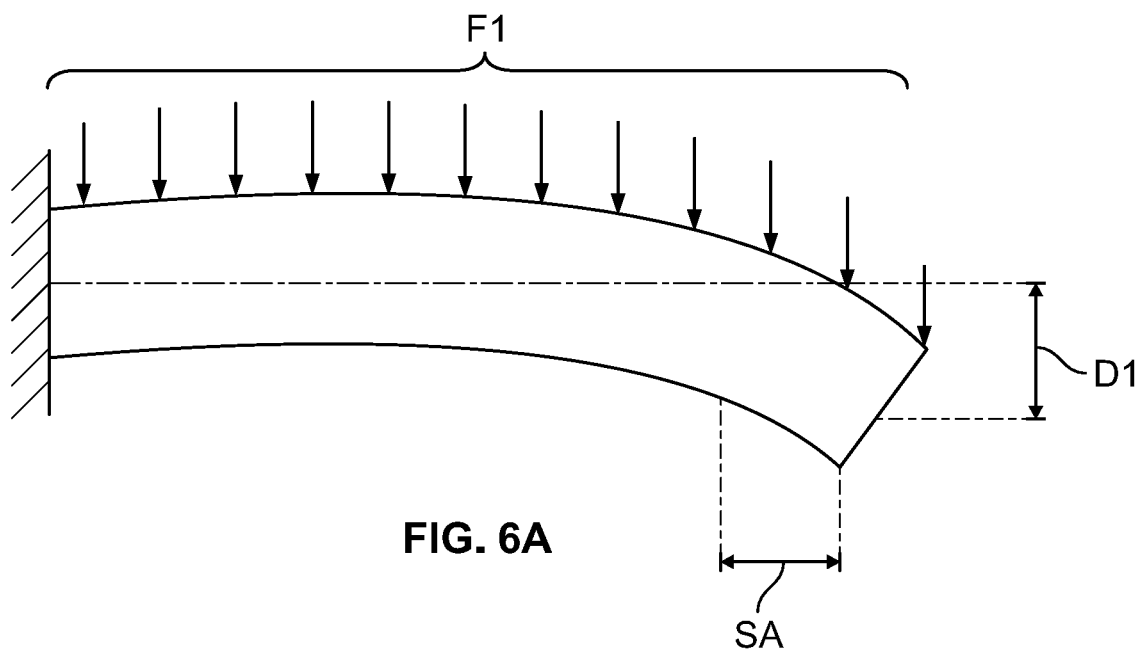
FIG. 6A is a diagram of forces acting on the stent of the prosthetic heart valve of FIG. 3B.
Figure 6B:
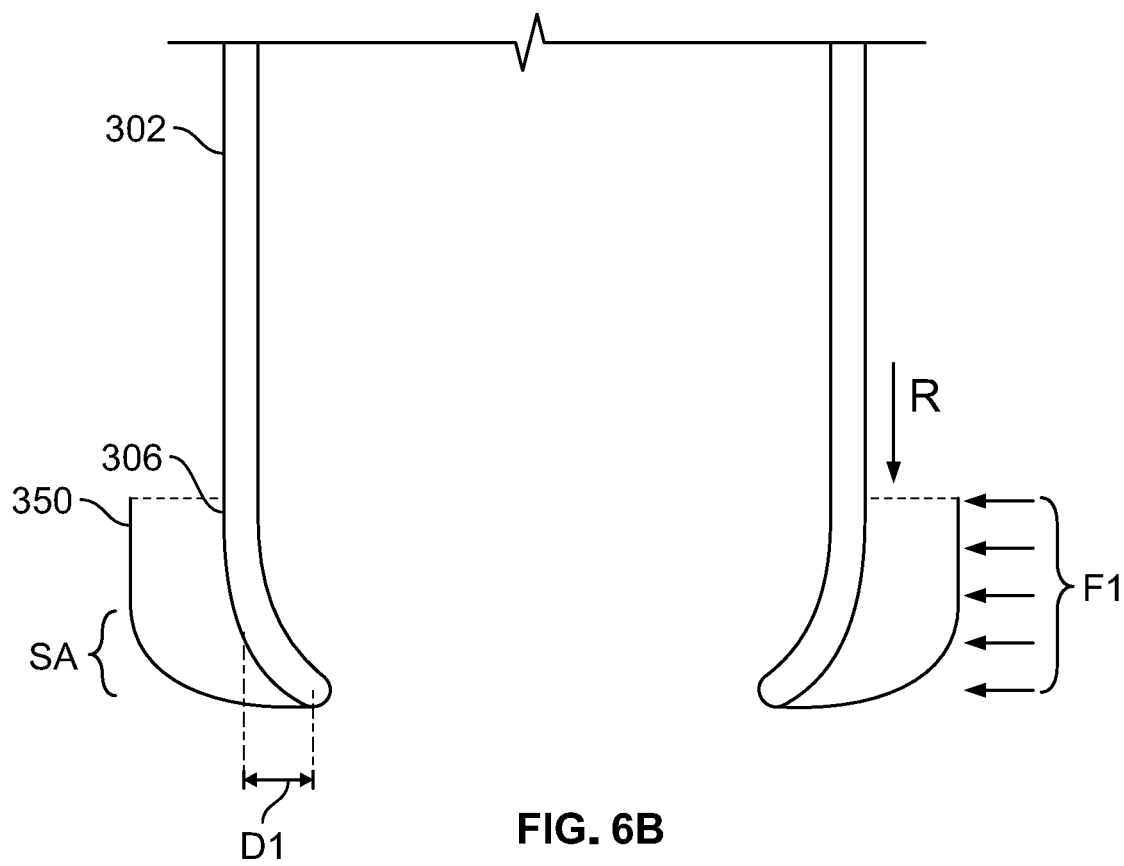
FIG. 6B is a highly schematic representation of deflection of the stent of the prosthetic heart valve of FIG. 3B due to the forces diagrammed in FIG. 6A.
Figure 7A:
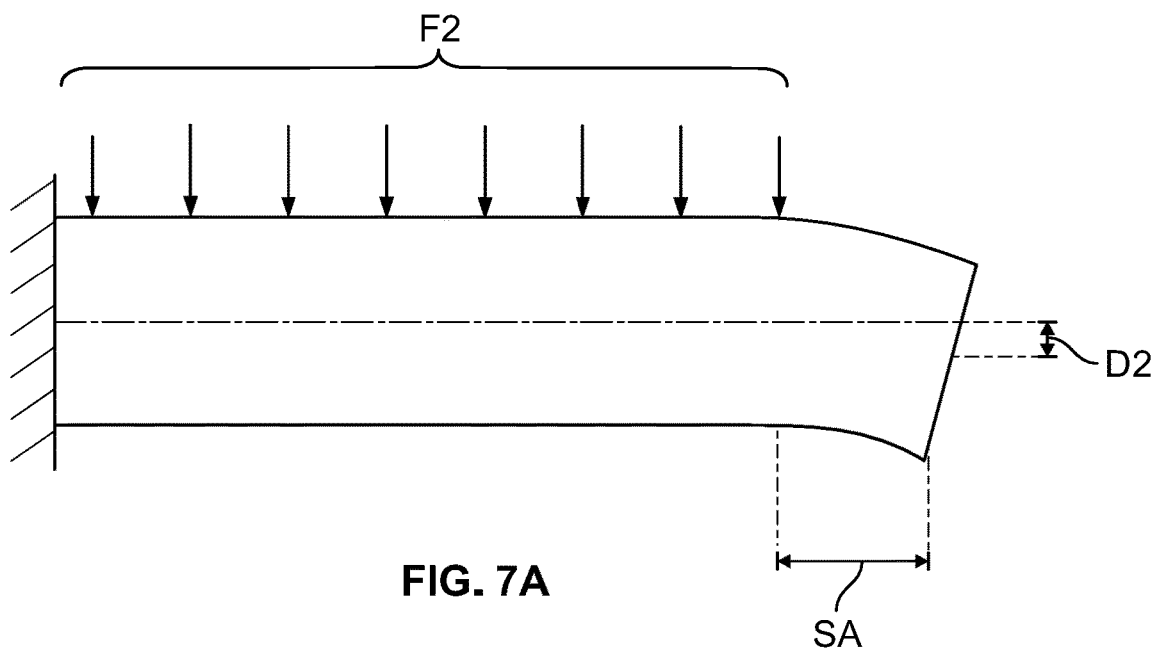
FIG. 7A is a diagram of forces acting on the stent of the prosthetic heart valve of FIG. 5A.
Figure 7B:
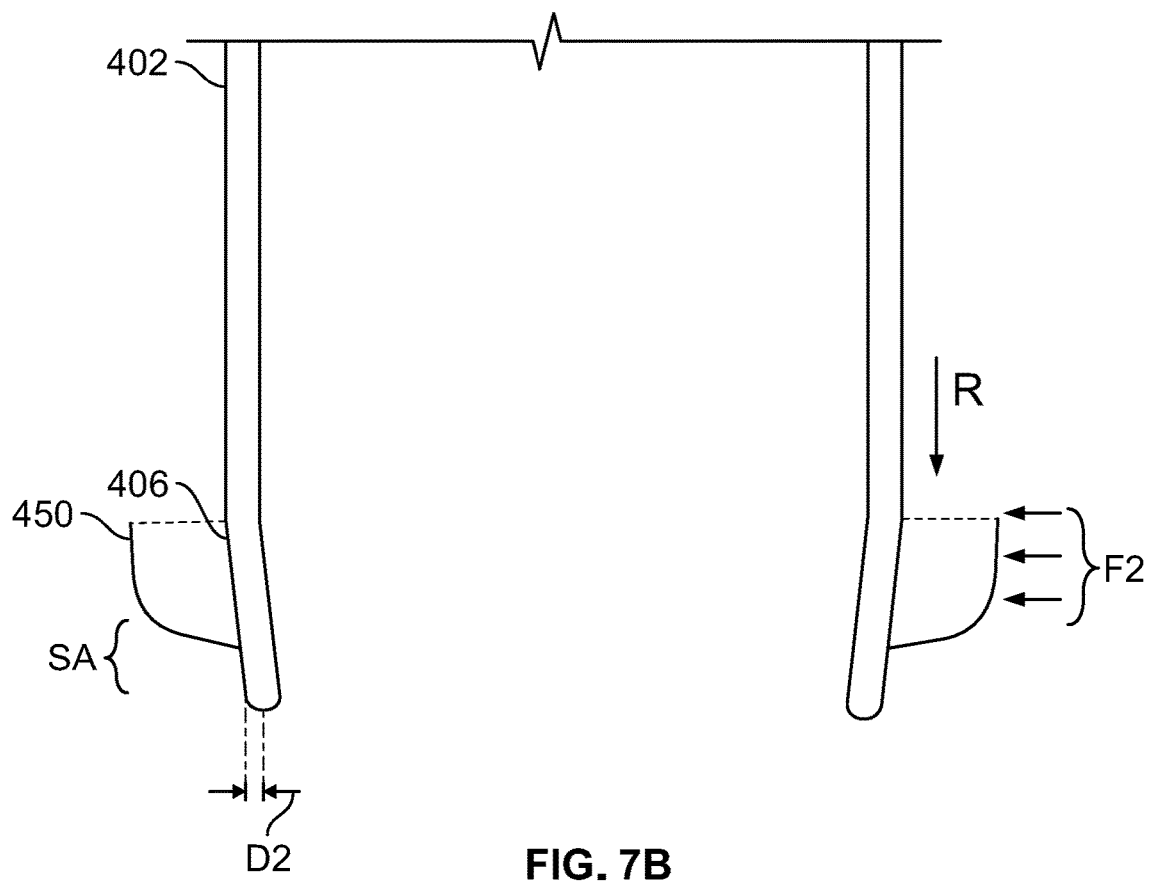
FIG. 7B is a highly schematic representation of deflection of the stent of the prosthetic heart valve of FIG. 5A due to the forces diagrammed in FIG. 7A.

FIGS. 6A and 6B show that, as blood flows in the retrograde direction R into the space between inner cuff 306 and outer cuff 350, forces F1 act radially inwardly in that area on the inner cuff and thus also the adjacent portions of stent 302, causing an amount of deflection D1. The relatively large deflection of stent 302 in the sub-annular portion SA, caused at least in part by a cantilever effect on the free inflow end of the stent, is illustrated by the diagram of FIG. 6A. On the other hand, as shown in FIGS. 7A-7B, the same retrograde blood flow applies radially inward force F2 over the portion of stent 402 spaced away from the terminal inflow edge, resulting in a reduced moment and lessened cantilever effect. While forces F2 may still cause some amount of deflection D2 in the proximalmost end of stent 402, the omission of radial inward forces being applied directly to the sub-annular portion SA of the stent results in a relatively small deflection compared to the deflection D1 expected in stent 302 when the remaining conditions are the same.

It should be understood that the forces and deflections shown in FIGS. 6A-7B are not expected to be static due to the pulsatile nature of blood flow. Stated otherwise, as the prosthetic heart valves 300, 400 open and close during the cardiac cycle, the forces and deflections shown in FIGS. 6A-7B would be cyclical, occurring while the prosthetic heart valve is in the closed condition and blood attempts to flow in the retrograde direction R between the abluminal surface of the prosthetic valve and the native valve annulus 250. This cyclical nature of the deflection may increase the stresses in stents 302, 402 and cause stent fatigue, which may reduce the overall amount of time during which the prosthetic heart valves 300, 400 are expected to function properly. The larger deflections D1 that may occur in prosthetic heart valve 300 may result in a corresponding shorter lifespan of the prosthetic heart valve compared to that of prosthetic heart valve 400.

It should be understood that the deflections D1 and D2 shown in FIGS. 6A-7B are not intended to be to scale or to otherwise represent actual amounts of deflection, but rather are intended to illustrate schematically that a smaller deflection D2 is expected in stent 402 compared to the larger deflection D1 expected in stent 302.

It may be possible to achieve similar or the same results of maintaining a suitable level of PV leak mitigation while reducing deflection-induced stent fatigue in manners other than that described in connection with FIGS. 5A-B.

Figure 8:
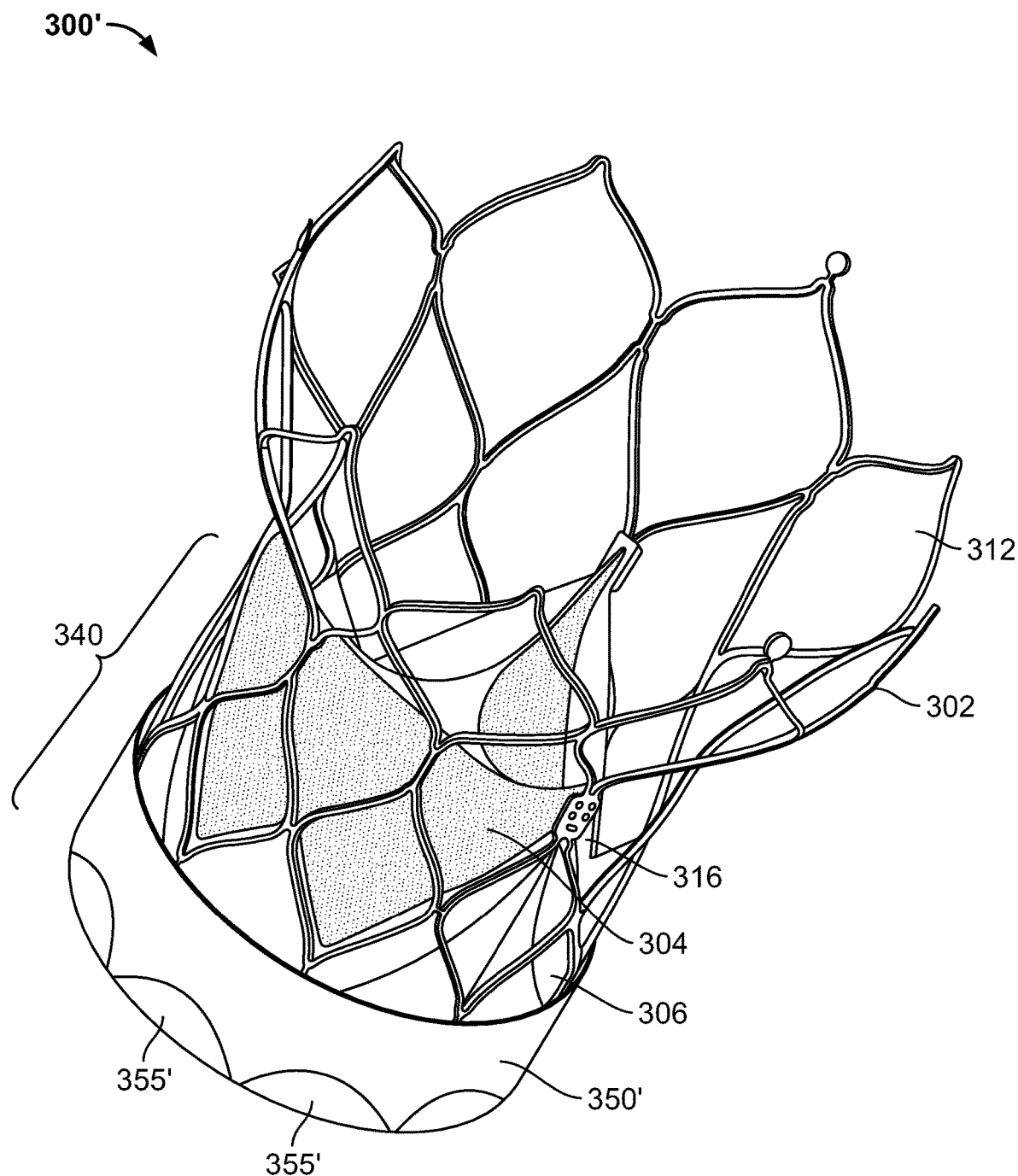
FIG. 8 is a perspective view of a prosthetic heart valve according to another aspect of the disclosure.

Referring now to FIG. 8, a prosthetic heart valve 300' is illustrated that is identical to prosthetic heart valve 300 with one exception. It should be understood that the part numbers in FIG. 8 that are identical to the part numbers in FIG. 3B indicate a similar or identical structure, and thus are not described in any further detail. The difference in prosthetic heart valve 300' is found in outer cuff 350'. Outer cuff 350' may be generally identical in shape, size, and positioning to outer cuff 350, but may be modified to decrease the available space between the outer cuff 350' and inner cuff 306 that is available to receive retrograde blood flow therebetween. In the particular embodiment illustrated in FIG. 8, one or more sutures (or other fasteners) 355' coupled the outer cuff 350' to the inner cuff 306 at positions near the terminal inflow end of the prosthetic heart valve 300'. As illustrated, one suture 355' (or one suture line) is provided for each cell 312 in the proximalmost row of cells. Each suture 355' (or each suture line) extends from the terminal inflow end of the outer cuff 350', and curves to reach its highest point near a circumferential center of the corresponding cell 312, at which point the suture 355' (or suture line) curves back down toward the terminal inflow end of the outer cuff 350'. Because the suture 355' couples the outer cuff 350' to the inner cuff 306, the space beneath the suture 355' (or suture line) is not available for blood to flow into. In other words, rather than physically shortening the outer cuff 350' to achieve a structure similar to outer cuff 450, the suture 355' effectively reduces the available area in which blood may flow, achieving a similar or identical effect without altering the height of outer cuff 350. Thus, any retrograde blood flowing into the available space between outer cuff 350' and inner cuff 306 will not be able to flow beyond the sutures 355', minimizing the amount of deflection that may be expected at the terminal inflow end of stent 302. It should be understood that a single suture may form the entire suture line 355' extending around the circumference of the stent 302, although more than one suture may be used to form the entirety of the suture line 355'.

In the particular embodiment of outer cuff 350' illustrated in FIG. 8, the peak of each suture 355' (or suture line) may generally axially align with the proximal apex of a cell 312 in the proximalmost row of cells. However, such alignment is not required, and the sutures 355' (or suture line) may be circumferentially offset compared to the embodiment illustrated in FIG. 8. This curved or scalloped shape, however, is not required. For example, a substantially straight suture or suture line may extend circumferentially around stent 312, attaching the outer cuff 350' to the inner cuff 306 at a point between about 3 mm and about 5 mm or about 6 mm from the inflow end of stent 302. Still further, sutures 355' are illustrated in FIG. 8 as being substantially continuous around the circumference of stent 302, but this is not required either. For example, sutures 355' may be strategically positioned to couple outer cuff 350' to inner cuff 306 at positions expected to be prone to the greatest amount of deflection. In one example, sutures 355' may be provided on the inflow end of outer cuff 350' in positions axially aligned with, or axially adjacent to, commissures attachment features 316. The areas of inner cuff 306 that are aligned with commissure attachment features 316 may be relatively high pressure areas, and thus the portions of the terminal inflow end of stent 302 that are axially aligned with (or axially adjacent to) the commissure attachment features 316 may be most likely to experience the undesirable deflection described above. Thus, reducing the available space between outer cuff 350' and inner cuff 306 at positions axially aligned with, or axially adjacent to, commissure attachment features 316 may provide similar functionality with fewer sutures 355' (or less total suture material) required.

Although the invention has been generally described in relation to a prosthetic heart valve for use to replace the functioning of the native aortic valve, it should be understood that the invention is not so limited. In other words, a prosthetic heart valve substantially similar to prosthetic heart valves 300' and/or 400 may be used to replace the functioning of a native pulmonary valve. Similarly, the concepts described above in connection with the structure of outer cuff 350' and/or the positioning of outer cuff 450 relative to a native valve annulus may be applied to prosthetic heart valves intended to replace the functioning of either the native mitral valve or native tricuspid valve. Despite these options, the configuration of outer cuff 350' and/or outer cuff 450 described above may be most useful in prosthetic heart valves that replace the functioning of the native valve of the left heart, as pressures involved with pumping blood in the left heart are typically significantly larger than forces at the valves of the right heart. However, it should also be understood that modifications may be appropriate if being used for a different valve. For example, if the concepts described above were implemented in a prosthetic mitral valve, certain elements may appropriately be modified to account for the different anatomy in the mitral valve compared to the aortic valve.

According to a first aspect of the disclosure, a prosthetic heart valve for replacing a native comprises:
  a stent extending in a longitudinal direction from an inflow end to an outflow end;
  a valve assembly disposed within the stent;
  a first cuff annularly disposed adjacent the stent; and
  a second cuff having a proximal edge facing toward the inflow end of the stent and a distal edge facing toward the outflow end of the stent, the second cuff being annularly disposed about the stent radially outward of the first cuff, the distal edge of the second cuff being coupled to at least one of the first cuff and the stent at a plurality of locations spaced apart in a circumferential direction of the stent to form at least one pocket between the first cuff and the second cuff, the proximal edge of the second cuff being coupled to at least one of the first cuff and the stent at a spaced distance from the inflow end of the stent; and/or
  the first cuff is positioned on an interior surface of the stent and the second cuff is positioned on an exterior surface of the stent; and/or
  the first cuff is coupled to the stent via one or more sutures; and/or
  the second cuff is coupled to both the first cuff and the stent; and/or
  the second cuff is coupled to the first cuff and the stent via one or more sutures; and/or
  the first cuff and the second cuff together define openings between adjacent ones of the plurality of locations; and/or
  each of the openings is in fluid communication with the at least one pocket; and/or
  the proximal edge of the second cuff is coupled to the at least one of the first cuff and the stent via a continuous suture line; and/or
  a first surface of the stent positioned between the proximal edge of the second cuff and the inflow end of the stent is uncovered; and/or
  a second surface of the stent opposite the first surface is positioned between the proximal edge of the second cuff and the inflow end of the stent, and is at least partially covered by the first cuff; and/or
  the spaced distance is between about 3 mm and about 6 mm.

According to a second aspect of the disclosure, a method of implanting a prosthetic heart valve into a valve annulus of a patient comprises:
  introducing the prosthetic heart valve into the valve annulus of the patient, the prosthetic heart valve including a stent, a valve assembly disposed within the stent, a first cuff annularly disposed adjacent the stent, and a second cuff annularly disposed on an exterior of the stent radially outward of the first cuff; and
  positioning the prosthetic heart valve in the valve annulus of the patient so that a sub-annular portion of the stent extends beyond the native valve annulus so that the sub-annular portion of the stent is not in direct contact with the native valve annulus, the sub-annular portion of the stent including an inflow end of the stent, a portion of the second cuff being in direct contact with the native valve annulus, and the sub-annular portion of the stent being uncovered by the second cuff; and/or
  the second cuff has a proximal edge facing toward the inflow end of the stent and a distal edge facing toward an outflow end of the stent, the distal edge of the second cuff being coupled to at least one of the first cuff and the stent at a plurality of locations spaced apart in a circumferential direction of the stent to form at least one pocket between the first cuff and the second cuff; and/or positioning the prosthetic heart valve in the valve annulus of the patient includes positioning the at least one pocket adjacent the valve annulus; and/or the proximal edge of the second cuff is coupled to at least one of the first cuff and the stent at a spaced distance from the inflow end of the stent toward the outflow end of the stent; and/or the first cuff and the second cuff together define openings between adjacent ones of the plurality of locations; and/or each of the openings is in fluid communication with the at least one pocket and is positioned so that retrograde blood flow around the exterior of the stent will tend to enter the at least one pocket through one or more of the openings to billow the second cuff outwardly toward the valve annulus of the patient; and/or the prosthetic heart valve is positioned in the valve annulus of the patient so that, upon the blood flowing into the at least one pocket, pressure from the blood flowing into the at least one pocket is not directly applied to the sub-annular portion of the stent in a direction toward a longitudinal center of the stent; and/or the sub-annular portion of the stent has a length of between about 3 mm and about 6 mm in a longitudinal direction of the stent; and/or the stent is a collapsible and expandable stent, and positioning the prosthetic heart valve in the valve annulus includes transitioning the stent from a collapsed condition to an expanded condition within the valve annulus.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. For example, features of one embodiment described above may be combined with features of other embodiments described above.

The invention claimed is:

1. A prosthetic heart valve for replacing a native valve, comprising:
   a stent extending in a longitudinal direction from an inflow end to an outflow end;
   a valve assembly disposed within the stent;
   a first cuff annularly disposed adjacent the stent; and
   a second cuff having a proximal edge facing toward the inflow end of the stent and a distal edge facing toward the outflow end of the stent, the second cuff being annularly disposed about the stent radially outward of the first cuff, the distal edge of the second cuff being coupled to at least one of the first cuff and the stent at a plurality of first locations spaced apart in a circumferential direction of the stent to form at least one pocket between the first cuff and the second cuff, the second cuff being coupled to the first cuff at a plurality of second locations positioned a spaced distance from the inflow end, such that areas proximal to the plurality of second locations between the first and second cuff are sealed against receiving retrograde blood flow therein and such that a sub-annular portion of the stent extending between the inflow end and the proximal edge of the second cuff is uncovered, wherein the uncovered sub-annular portion of the stent extends to a distance between about 3 mm and about 5 mm from the inflow end.

2. The prosthetic heart valve of claim 1, wherein the first cuff is positioned on an interior surface of the stent and the second cuff is positioned on an exterior surface of the stent.

3. The prosthetic heart valve of claim 1, wherein the first cuff is coupled to the stent via one or more sutures.

4. The prosthetic heart valve of claim 1, wherein the second cuff is coupled to both the first cuff and the stent.

5. The prosthetic heart valve of claim 1, wherein the second cuff is coupled to the first cuff and the stent via one or more sutures.

6. The prosthetic heart valve of claim 1, wherein the first cuff and the second cuff together define openings between adjacent ones of the plurality of locations.

7. The prosthetic heart valve of claim 6, wherein each of the openings is in fluid communication with the at least one pocket.

8. The prosthetic heart valve of claim 1, wherein the second cuff is coupled to the first cuff at the plurality of second locations by a single continuous suture line.

9. The prosthetic heart valve of claim 1, wherein the second cuff is coupled to the first cuff at the plurality of second locations by a suture line.

10. The prosthetic heart valve of claim 9, wherein the suture line includes a plurality of individual suture lines, each individual suture line being aligned with a corresponding cell of the stent.

11. The prosthetic heart valve of claim 10, wherein each individual suture line is curved to form a central peak.

12. A method of implanting a prosthetic heart valve into a valve annulus of a patient, the method comprising:
   introducing the prosthetic heart valve into the valve annulus of the patient, the prosthetic heart valve including a stent, a valve assembly disposed within the stent, a first cuff annularly disposed adjacent the stent, and a second cuff annularly disposed on an exterior of the stent radially outward of the first cuff, the second cuff having a proximal edge facing toward an inflow end of the stent and a distal edge facing toward an outflow end of the stent, the distal edge of the second cuff being coupled to at least one of the first cuff and the stent at a plurality of first locations spaced apart in a circumferential direction of the stent to form at least one pocket between the first cuff and the second cuff, the second cuff being coupled to the first cuff at a plurality of second locations positioned a spaced distance from the inflow end, such that areas proximal to the plurality of second locations between the first and second cuff are sealed against receiving retrograde blood flow therein and such that a sub-annular portion of the stent extending between the inflow end and the proximal edge of the second cuff is uncovered; and
   positioning the prosthetic heart valve in the valve annulus of the patient so that the sub-annular portion of the stent extends beyond the native valve annulus so that the sub-annular portion of the stent is not in direct contact with the native valve annulus, the sub-annular portion of the stent including the inflow end of the stent and the areas proximal to the plurality of second locations between the first and second cuff that are sealed against receiving retrograde blood flow therein, wherein the sub-annular portion has a length from about 3 mm to about 6 mm.

13. The method of claim 12, wherein positioning the prosthetic heart valve in the valve annulus of the patient includes positioning the at least one pocket adjacent the valve annulus.

14. The method of claim 12, wherein the first cuff and the second cuff together define openings between adjacent ones of the plurality of first locations.

15. The method of claim 14, wherein each of the openings is in fluid communication with the at least one pocket and is positioned so that retrograde blood flow around the exterior of the stent will tend to enter the at least one pocket through one or more of the openings to billow the second cuff outwardly toward the valve annulus of the patient.

16. The method of claim 15, wherein the prosthetic heart valve is positioned in the valve annulus of the patient so that, upon the blood flowing into the at least one pocket, pressure from the blood flowing into the at least one pocket is not directly applied to the sub-annular portion of the stent in a direction toward a longitudinal center of the stent.

17. The method of claim 12, wherein the stent is a collapsible and expandable stent, and positioning the prosthetic heart valve in the valve annulus includes transitioning the stent from a collapsed condition to an expanded condition within the valve annulus.

18. A prosthetic heart valve for replacing a native valve, comprising:

a stent extending in a longitudinal direction from an inflow end to an outflow end;
a valve assembly disposed within the stent;
a first cuff annularly disposed adjacent the stent; and
a second cuff having a proximal edge facing toward the inflow end of the stent and a distal edge facing toward the outflow end of the stent, the second cuff being annularly disposed about the stent radially outward of the first cuff, the distal edge of the second cuff being coupled to at least one of the first cuff and the stent at a plurality of first locations spaced apart in a circumferential direction of the stent to form at least one pocket between the first cuff and the second cuff, the second cuff being coupled to the first cuff at a plurality of second locations positioned a spaced distance from the inflow end, such that areas proximal to the plurality of second locations between the first and second cuff are sealed against receiving retrograde blood flow therein and such that a sub-annular portion of the stent extending between the inflow end and the proximal edge of the second cuff is not subjected to retrograde blood flow through the second cuff when the prosthetic heart valve is implanted into a valve annulus of a patient, wherein the uncovered sub-annular portion of the stent extends to a distance between about 3 mm and about 5 mm from the inflow end.

\* \* \* \* \*